United States Patent [19]

Demer et al.

[11] Patent Number: 4,651,738

[45] Date of Patent: Mar. 24, 1987

[54] METHOD AND DEVICE FOR PERFORMING TRANSLUMINAL ANGIOPLASTY

[75] Inventors: Linda L. Demer; Avanindra Jain; Albert E. Raizner; Craig J. Hartley, all of Houston, Tex.

[73] Assignee: Baylor College of Medicine, Houston, Tex.

[21] Appl. No.: 762,081

[22] Filed: Aug. 2, 1985

[51] Int. Cl.$^4$ .................................................. A61M 29/02
[52] U.S. Cl. ................................... 128/344; 128/348.1
[58] Field of Search ............... 128/325, 344, 348.1, 128/1 D, 675, DIG. 25; 604/97, 98, 100

[56] References Cited

U.S. PATENT DOCUMENTS

| | | | |
|---|---|---|---|
| 3,834,394 | 9/1974 | Hunter et al. | 128/325 |
| 4,332,254 | 6/1982 | Lundquist | 128/344 |
| 4,370,982 | 2/1983 | Reilly | 604/98 |
| 4,446,867 | 5/1984 | Leveen et al. | 128/344 |

Primary Examiner—Carlton R. Croyle
Assistant Examiner—Theodore W. Olds
Attorney, Agent, or Firm—Fulbright & Jaworski

[57] ABSTRACT

A novel method and device for performing percutaneous transluminal angioplasty to treat occlusive artery disease is disclosed. The method involves simultaneous measurement and display of the fluid pressure and volume existing within the balloon catheter as the procedure is performed. Information is produced which is useful in determining the efficacy of the procedure as it is performed which obviates the need for arbitrary repeated inflations. The information is also useful in the subsequent management of the patient's disease.

5 Claims, 4 Drawing Figures

METHOD AND DEVICE FOR PERFORMING TRANSLUMINAL ANGIOPLASTY

BACKGROUND OF THE INVENTION

1. Field of the Invention

The present invention constitutes an improved technique for performing percutaneous transluminal angioplasty. Angioplasty is a medical procedure used to treat patients whose arteries have become occluded due to the disease process call atherosclerosis.

Arteriosclerosis is a general term which refers to any of a group of diseases in which the lumen of an artery becomes narrowed or blocked. The most common and important form of arteriosclerosis, especially in Western societies, is the disease known as atherosclerosis. In atherosclerosis, there is an accumulation of lipids in the intimal, or inner, layer of the affected artery. The resulting intimal thickening restricts the flow of blood so as to hinder the functioning of, or permanently damage, the organ which the artery feeds. These accumulations of lipids tend to be localized and can occur in coronary, cerebral, or peripheral arteries. They will hereinafter be referred to synonymously as lesions, plaques, or atheromas.

The lipid accumulation is made up of free lipid and smooth muscle cells which have proliferated and taken up lipid. As the disease progresses, the lesion may begin to absorb calcium which causes it to harden and may also be composed of blood which has clotted in response to the presence of the atheroma. Although the process of plaque formation is not completely understood, it is known to be progressive, and atherosclerotic plaques may vary greatly in their physical characteristics.

Treatment of atherosclerosis is aimed at alleviating the diminished blood flow. This can sometimes be done by medical means which cause the smooth muscles of the arterial walls to relax and thereby dilate the artery. Other treatment methods are directed toward physiological compensation for the reduced blood flow. In cases where the artery is severely occluded, however, there is no reasonable alternative but to try to re-establish a lumen of proper diameter. A number of surgical procedures have been developed toward this end. These include endarterectomy, in which the plaque is surgically removed, and by-pass grafts, in which a segment of artery or vein from elsewhere in the body is removed and reattached in place of the occluded artery. These procedures are major surgical operations and present a number of disadvantages to a patient including financial cost, inconvenience, and the risk of complications associated with any major surgery. Therefore, in the past several years, methods of re-establishing the patency of an occluded artery have been developed which are relatively non-invasive and present less risk to a patient than conventional surgery. One such method is transluminal angioplasty.

2. Description of the Prior Art

The conventional method of performing transluminal angioplasty uses a special double lumen catheter. The first, or inner, lumen allows passage of a guide wire. Concentric with this lumen is a second lumen which connects to a sausage-shaped segment or balloon at the distal end of the catheter. The second lumen and balloon are generally filled with diluted contrast media. Contrast media is radio-opaque liquid which makes visualization of the catheter possible by means of X-rays. The procedure first involves selecting a convenient place to introduce the catheter into the arterial system of the patient, such as the femoral artery of the leg. Next, the catheter is guided to the blocked artery. This is done manually and with the aid of an X-ray monitor. When the catheter is appropriately positioned, the guide wire is advanced to and past the point of obstruction. The balloon catheter, which surrounds the guide wire, is then advanced along with the guide wire until it is surrounded by the occluding plaque. The balloon, made of material with high tensile strength and low elasticity, is inflated to a pressure as high as twelve atmospheres. As the balloon expands it creates a larger inner diameter within the occluded artery. It is not known with certainty what physical processes occur within the occluded artery in response to the balloon inflation, but the usual method is to inflate the balloon to a certain predetermined pressure and repeat the inflation an arbitrary number of times. The balloon is then collapsed and retracted. The site of the obstruction is then examined angiographically and, if the artery is still occluded, a decision is made either to repeat the angioplasty procedure or to resort to some other option.

As aforementioned, the procedure involves inflating the balloon to a predetermined pressure. Although the operator may observe the size of the balloon during the inflation by means of the X-ray monitor, unless the pressure is measured, the bursting pressure of the balloon may be exceeded causing rupture. Therefore, practitioners have realized the need for continuous monitoring of the fluid pressure within the balloon. As it is conventional to inject fluid into the balloon with a syringe, the most obvious method is to interpose a T-fitting between the delivery end of the syringe and the balloon catheter. A standard pressure transducer can then be connected to the T-fitting and the fluid pressure within measured. U.S. Pat. No. 4,370,982 discloses a method for measuring fluid pressure without the transmitter coming in contact with the working medium. The '982 patent also discloses an injection device which uses a threaded member which when rotated produces translational motion of the syringe plunger. The relatively slow inflation is supposed to reduce further the risk of balloon rupture.

Another relevant patent is U.S. Pat. No. 4,446,867 which discloses a method and apparatus for generating pulses of pressure within the balloon catheter. As discussed above, some atheromas become hard due to calcification and therefore resist dilation by the balloon. The '867 patent represents an attempt to deal with this problem by inflating the balloon so rapidly that the plaque is broken. Although the specification of the '867 patent recites that pieces of broken plaque will be removed by normal cardiovascular processes, it seems obvious that such fragments may flow downstream and become lodged in a smaller artery, thereby completely blocking blood flow. As pieces of plaque may break off during conventional angioplasty procedures, even without using the pulsed pressure method of the '867 patent, it is important to know when this has occurred so that remedial steps may be taken.

SUMMARY OF THE INVENTION

One major problem with transluminal angioplasty is that there has heretofore been no means of evaluating the efficacy of the procedure contemporaneous with the performing of it. This has resulted in the establishment of arbitrary performance protocols whereby the balloon is inflated repeatedly an arbitrary number of times. Because the pressures involved are necessarily high, each subsequent inflation presents a risk of balloon rupture. It would be advantageous if the operator had some means of judging when the procedure had succeeded or failed and whether a subsequent inflation could be expected to succeed. As atherosclerotic plaques vary greatly in their physical characteristics, what is needed is a means of monitoring the underlying physical events occurring within the occluded artery as the balloon in inflated. Not only would this be helpful during the performance of the procedure itself, but it would make possible a more accurate prognosis of the course of the patient's disease and aid in evaluating other treatment options.

The present invention accomplishes this objective by providing for the simultaneous monitoring of both pressure and volume changes occurring within the balloon as the angioplasty procedure is performed. By the use of basic physical principles, the pressure-volume curves thus generated can be correlated with the physical changes taking place within the occluded artery.

DESCRIPTION OF THE INVENTION

Figure 4:
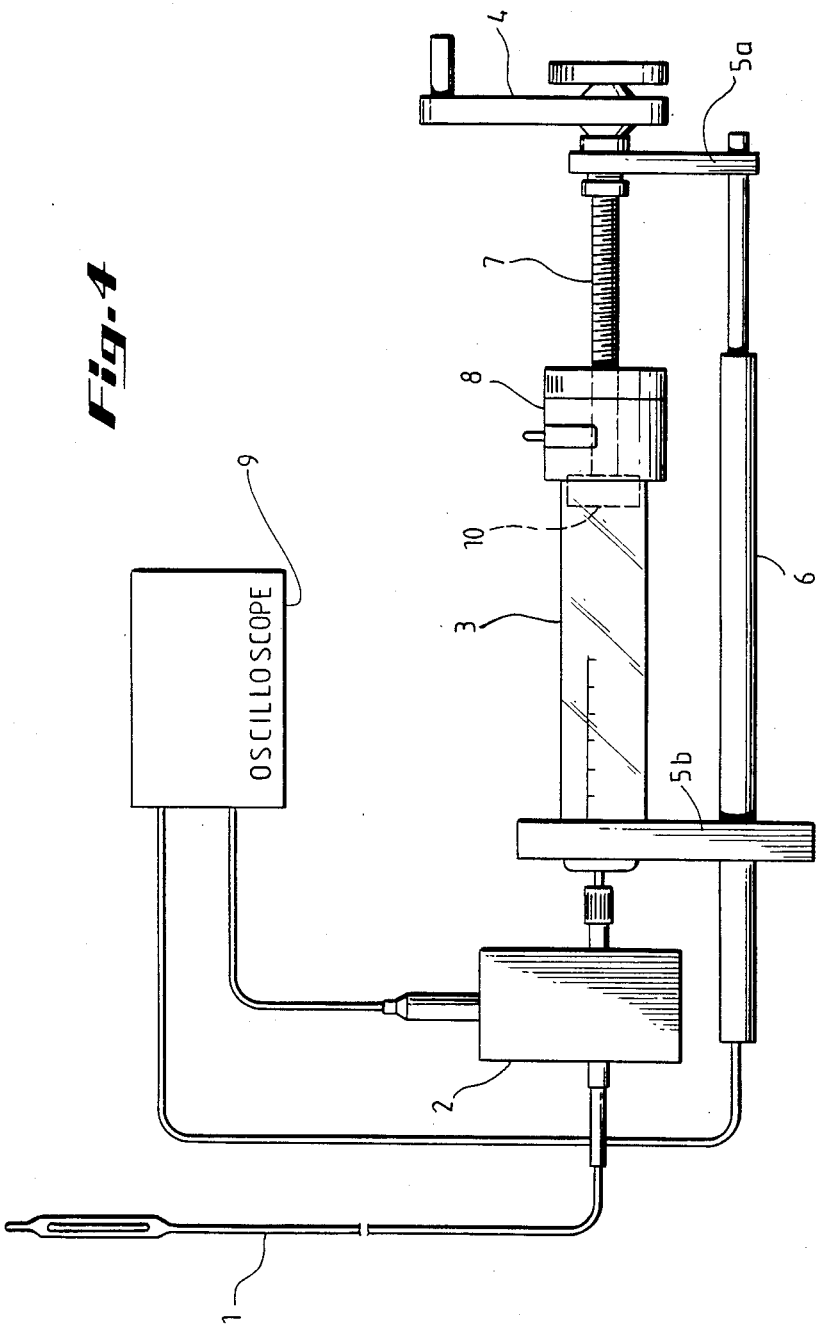
FIG. 4 is a drawing of the device used to perform the angioplasty procedure in accordance with the present invention.

The best mode and preferred embodiment of the invention is illustrated in FIG. 4. The proximal end of the balloon catheter 1 is attached to the inflation syringe 3. The syringe is of standard type but modified for reasons which will be apparent below. A plunger 10 moves through the barrel of the syringe 3 displacing liquid, such as diluted contrast media, into the balloon catheter 1. The plunger shaft 7 is finely threaded all along its length so that when turned, the shaft moves longitudinally through an oppositely threaded annular member 8. The annular member 8 is attached to the syringe 3. In this way, slow and even displacement of liquid into the balloon catheter is produced by rotating the shaft 7. The more fine the threads, of course, the slower will be the fluid displacement. A hand crank 4 has been added to facilitate the balloon inflation process.

Interposed between the balloon catheter 1 and inflation syringe 3 is an electronic pressure transducer 2 of conventional type. An electronic signal proportional to the fluid pressure existing within the catheter is then fed to an oscilloscope 9 for real-time display. Any type of electronic recording device could also be used. A linear displacement transducer 6, which produces an electronic signal proportional to its length at any given time also feeds into the oscilloscope 9. The ends of the linear displacement transducer 6 are connected by means of coupling bars 5a and 5b to the plunger shaft 7 and inflation syringe 3 respectively. In this way the signal produced by the linear displacement transducer 6 is proportional to the volume of fluid displaced from the syringe 3 and hence residing in the balloon catheter 1. Thus, there are two electronic signals fed to the oscilloscope 9 which represent the volume and pressure of the fluid contained by the balloon at any given time. By displaying the pressure and volume inputs simultaneously a curve is generated by the oscilloscope wherein one axis corresponds to pressure and the other axis corresponds to volume. The information contained in this curve enables one to draw certain conclusions regarding the physical process taking place during the dilation process as will now be explained.

Figure 1:
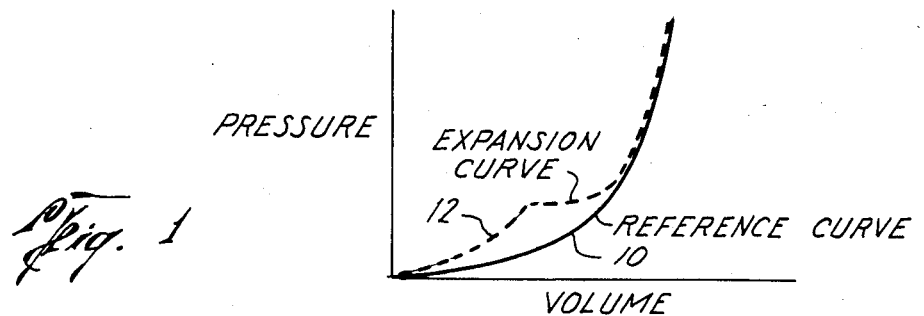
FIG. 1 depicts the pattern of a typical pressure-volume curve generated when an expanding balloon compacts or compresses the plaque material against the artery wall.
Figure 2:
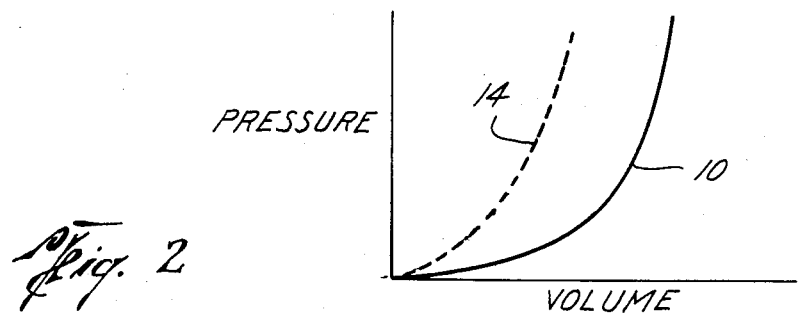
FIG. 2 depicts the pattern of a typical pressure-volume curve generated when an expanding balloon stretches the artery wall itself.
Figure 3:
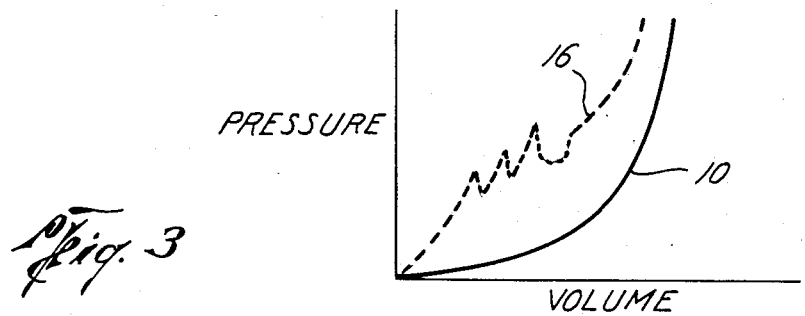
FIG. 3 depicts the pattern of a typical pressure-volume curve generated when an expanding balloon causes fractures in a plaque composed of relatively rigid material.

FIGS. 1–3 depict expansion curves generated by dilating models of arterial lesions with three different types of behavior. Superimposed on all three figures is the expansion curve 10 of the balloon expanded by itself. This represents the compliance of the balloon alone and will be used as the reference curve.

Referring first to FIG. 1, expansion curve 12 shows that as the pressure is raised initially, there is little change in the volume of the balloon as compared with the reference curve 10. This indicates that the atherosclerotic plaque which surrounds the balloon is preventing the balloon from expanding. As the pressure is increased further, however, the pressure within the balloon becomes great enough to overcome the resistance of the plaque material. At this point the occluded artery begins to dilate as the balloon expands. It is not clear whether the plaque material is actually compressed so as to occupy less volume or is deformed so as to be redistributed along the length of the artery, but what is important is that the expansion takes place at relatively constant pressure. At any given point along the curve, the pressure of the fluid within the balloon is exactly balanced by the pressure exerted by the surrounding plaque. A region of constant pressure, or isobaric, expansion indicates that the plaque material is exerting the same force irrespective of the extent of the plaque's deformation. The theory of the properties of materials would predict that the stress exerted on the plaque had exceeded the yield point of the plaque material. This would mean that the plaque material is being deformed plastically rather than elastically. This is consistent with a young or at least still malleable atheroma which can be expected to retain the deformation produced by the expanded balloon. Thus, when an expansion curve like that of FIG. 1 is obtained, the operator may infer that the angioplasty procedure has been relatively successful and no further inflation cycles are necessary, especially if a repeat inflation yields a curve superimposed on curve 10. Furthermore, the knowledge that the atheroma responded to the procedure in this way is useful in the subsequent management of the patient's atherosclerotic disease.

Next, in FIG. 2, is an expansion curve 14 which indicates that as the balloon expands against the occluded artery, the artery exerts increasing force against the balloon. This would lead one to conclude that the occluded artery is acting like a spring and storing the work of expansion only to return to its former occluded shape when the balloon is deflated. This has been found experimentally to be the case although with repeated inflations the curve sometimes moves closer to the reference curve indicating that the artery is becoming more compliant. Unlike the case in FIG. 1, the atheroma in this example has probably been deformed very little by the expanding balloon. Since plaque is known not to be composed of elastic, or energy storing, material the likely source of the elasticity is the medial layer of the arterial wall itself. In any case, an expansion curve like that in FIG. 2 indicates a less desirable result for the patient than that in the first example above. The increased compliance of the arterial wall following repeated inflations may also indicate plastic changes such as thinning and microscopic tearing, such that it would be hazardous to try another inflation cycle.

Finally, FIG. 3 shows an expansion curve 16 exhibiting sharp drops in pressure as the balloon expands. A sudden decrease in the pressure exerted against the balloon by the occluded artery can only mean that a stress relieving fracture of some kind has occurred. One can then infer that the plaque was hard and brittle, presumably due to calcification, and was fractured by the expanding balloon. Not only does this indicate that angioplasty is not likely to be successful in dilating the artery, but remedial steps may need to be taken to prevent the plaque fragments from separating from the rest of the plaque causing complications at some point downstream. One such remedial step might be to inflate the balloon a second time, although at a lower pressure, in order to "tack" the plaque fragments down and prevent their dislodgment. Anticoagulant therapy may also be indicated.

In generating the expansion curves discussed above, the particular instrumentation used must be able to respond to the extremely small changes in volume involved when the balloon expands as well as pressures reaching twelve atmospheres. The inflation syringe described in the preferred embodiment was also constructed with a shaft possessing screw-type threads fine enough so that many rotations are necessary to move the shaft through the oppositely threaded annular member. A slow and even displacement of fluid into the balloon is necessary to avoid introducing artifacts into the pressure signal and obscuring the information contained therein. That is, a properly constructed expansion curve only contains pressure values which have been obtained after any transient pressure waves in the fluid have died out.

It should be understood that the embodiment disclosed hereinabove is not meant to limit the invention in any manner. On the contrary, it is intended to cover all modifications, alternatives, and equivalents as may be included within the spirit and scope of the invention as defined by the following claims.

What is claimed is:

1. An apparatus for performing, and characterizing the results of, a transluminal angioplasty procedure comprising:
   a balloon catheter means;
   a means for filling said balloon catheter means with liquid;
   a means for measuring the liquid pressure existing within said balloon catheter means;
   a means for measuring the volume of liquid contained within said balloon catheter means;
   a means for displaying present and past values of the liquid pressure and volume existing within said balloon catheter means.

2. An apparatus for performing, and characterizing the results of, a transluminal angioplasty procedure comprising:
   a balloon catheter means;
   a liquid supply means adapted to fill said balloon catheter means with liquid, said liquid supply means being connected to the distal end of said balloon catheter means and comprising a cylinder means and a piston means movably mounted in said cylinder means in order to positively displace liquid from said cylinder means to said balloon catheter means;
   a means for measuring the volume of liquid displaced by said piston means from said cylinder means into said balloon catheter means wherein said means comprises a linear displacement transducer which produces an electrical signal proportional to the distance between the end of said cylinder means which is connected to the distal end of said catheter means and the end of said piston means which is in contact with liquid, said linear displacement transducer means being physically connected to the cylinder means and the piston means;
   a means for measuring the liquid pressure inside said cylinder means and said balloon catheter means wherein said means comprises a pressure transducer which produces an electrical signal proportional to the liquid pressure and being physically connected to said liquid between said balloon means and said cylinder means;
   a means for displaying the electrical signals produced by said linear displacement transducer means and said pressure transducer means wherein said electrical signals are displayed simultaneously in analog form on separate axes of the display medium.

3. The apparatus of claim 2 wherein said piston means further comprises a threaded shaft connected to the end of said piston means which is not in contact with fluid, wherein said threaded shaft means is rotatably mounted in an oppositely threaded bore hole means which is physically connected to said cylinder means, and wherein said threaded shaft means moves longitudinally through said bore hole means when said shaft is rotated.

4. The apparatus of claim 3 wherein the threads of said threaded shaft and bore hole are constructed so finely that manual rotation of said threaded shaft displaces liquid slowly enough that no transient pressure waves are produced within the liquid.

5. A method for performing and characterizing the results of a transluminal angioplasty procedure comprising the steps of:
   injecting fluid into said balloon catheter means at a rate slow enough so as not to produce any transient variations in the relationship between the volume and the pressure of the fluid within said balloon catheter means;
   independently measuring the pressure and volume existing within said balloon catheter means and producing electrical signals proportional to said pressure and volume;
   displaying said electrical signals simultaneously in analog form on separate axes of the display.

* * * * *